United States Patent
Tang-Liu et al.

(10) Patent No.: US 10,736,885 B2
(45) Date of Patent: *Aug. 11, 2020

(54) COMPOSITIONS AND METHODS OF TREATING DERMAL FIBROTIC DISORDERS

(71) Applicant: AiViva BioPharma, Inc., Las Vegas, NV (US)

(72) Inventors: Diane Tang-Liu, Las Vegas, NV (US); Tiffany Liu, Las Vegas, NV (US)

(73) Assignee: AIVIVA BIOPHARMA, INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/767,137

(22) PCT Filed: Oct. 7, 2016

(86) PCT No.: PCT/US2016/055865
§ 371 (c)(1),
(2) Date: Apr. 9, 2018

(87) PCT Pub. No.: WO2017/062694
PCT Pub. Date: Apr. 13, 2017

(65) Prior Publication Data
US 2019/0070160 A1 Mar. 7, 2019

Related U.S. Application Data

(60) Provisional application No. 62/238,309, filed on Oct. 7, 2015.

(51) Int. Cl.
| | |
|---|---|
| A61K 31/454 | (2006.01) |
| A61K 31/404 | (2006.01) |
| A61K 31/47 | (2006.01) |
| A61K 31/506 | (2006.01) |
| A61K 31/4439 | (2006.01) |
| A61K 31/496 | (2006.01) |
| A61K 31/44 | (2006.01) |
| A61K 31/5025 | (2006.01) |
| A61P 17/02 | (2006.01) |
| A61K 31/497 | (2006.01) |

(52) U.S. Cl.
CPC .......... *A61K 31/454* (2013.01); *A61K 31/404* (2013.01); *A61K 31/44* (2013.01); *A61K 31/4439* (2013.01); *A61K 31/47* (2013.01); *A61K 31/496* (2013.01); *A61K 31/497* (2013.01); *A61K 31/506* (2013.01); *A61K 31/5025* (2013.01); *A61P 17/02* (2018.01)

(58) Field of Classification Search
CPC .. A61K 31/454; A61K 31/5025; A61K 31/44; A61K 31/496; A61K 31/4439; A61K 31/506; A61K 31/497; A61K 31/47; A61K 31/404; A61P 17/02; A61P 17/00
See application file for complete search history.

(56) References Cited

U.S. PATENT DOCUMENTS

| | | | |
|---|---|---|---|
| 2006/0142373 A1* | 6/2006 | Park | A61K 31/551 514/414 |
| 2008/0003219 A1 | 1/2008 | Peyman | |
| 2013/0210733 A1 | 8/2013 | Morgans, Jr. et al. | |

FOREIGN PATENT DOCUMENTS

| | | | | |
|---|---|---|---|---|
| WO | WO-0102369 A2 * | 1/2001 | | C07D 209/18 |
| WO | 2011060079 A1 | 5/2011 | | |
| WO | 2011147810 A1 | 12/2011 | | |
| WO | 2015005985 A1 | 1/2015 | | |

OTHER PUBLICATIONS

U.S. Appl. No. 16/485,221, filed Feb. 2017, Tang-Liu et al.*
Tsuzuki et al. Histopathology 2014, 64, 484 (Abstract). (Year: 2014).*
Jain et al. Lancet Haemotol. 2015, 2, e376 (Year: 2015).*
European Medicines Agency, Public Summary of Opinion on Orphan Designation, Riociguat for the Treatment of Systemic Sclerosis, Science Medicines Health, Aug. 27, 2014.
Seschka, S. et al., "Souble Guanylate Cyclase Stimulation Prevents Fibrotic Tissue Remodeling and Improves Survival in Salt-Sensitive Dahl Rats", PLos One, vol. 6, Issue 7, e21853, Jul. 18, 2011.
International Search Report & Written Opinion, of PCT/US2016/055865, dated Dec. 20, 2016.
Kavian, Niloufar et al., "Sunitinib Inhibits the Phosphorylation of Platelet-Derived Growth Factor Receptor Beta in the Skin of Mice with Scleroderma-like Features and Prevents the Development of the Disease", Arthritis & Rehumatism, vol. 64, No. 6, Jun. 1, 2012, pp. 1990-2000.
Huang, Jingang et al_, "Nintedanib Ameliorates Fibrotic and Vascular Manisfestations in Preclinical Models of Systemic Sclerosis", Arthritis & Reheumatology, vol. 67, No. Suppl. 10, Sep. 29, 2015, p. 2153.

(Continued)

*Primary Examiner* — Amanda L. Aguirre
(74) *Attorney, Agent, or Firm* — Maschoff Brennan; Brent A. Johnson; David W. Old

(57) ABSTRACT

A method for preventing and/or modulating formation of a dermal fibrotic disorder includes administering a therapeutically effective amount of a multi-phase modulator to a subject in need thereof. The multi-phase modulator is selected from the group consisting of axitinib, nintedanib, sorafenib, sunitinib, lenvatinib, panatinib, pazopanib, regorafenib, and riociguat. The dermal fibrotic disorder is acne scars, skin scars such as keloids and hypertrophic scars, wrinkles, cellulite and dermal neoplastic fibrosis, scarring alopecia, various vasculopathy, vasculitis, burn wound healing, diabetic foot syndrome, scleroderma, arthrofibrosis, peyronie's disease, dupuytren's contracture, or adhesive capsulitis.

17 Claims, 4 Drawing Sheets

(56) References Cited

OTHER PUBLICATIONS

Ota, Yuko et al., "Pirfenidone and BIBF1120 Suppress Collagen Synthesis in Skin Fibroblast from Patients with Systemic Sclerosis", Arthritis & Rheumatism, vol. 65, No. Suppl. 10, Oct. 2013, p. S280.
European Search Report, Application No. 16854374.2, dated Jul. 24, 2019.

* cited by examiner (A)  Control unwounded skin (B) Untreated wound center section (C) Axitinib-treated wound center section A. H&E Staining, 10X B. Mason's Trichrome Staining, 10X

COMPOSITIONS AND METHODS OF TREATING DERMAL FIBROTIC DISORDERS

CROSS REFERENCE TO RELATED APPLICATIONS

This claims the benefits of U.S. Provisional Patent Application No. 62/238,309, filed on Oct. 7, 2015, the disclosure of which is incorporated by reference in its entirety.

TECHNICAL FIELD

This invention relates to compositions and methods for preventing or treating formation of fibrotic lesions, including skin scars such as keloids and hypertrophic scars.

BACKGROUND

Dermal wound healing involves several phases: hemostasis, inflammation, proliferation, and tissue maturation. The overall process is induced and regulated by a complex array of factors, such as growth factors and cytokines.

The initial hemostasis controls the release of a variety of growth factors and/or cytokines from activated platelets to promote blood clotting. The hemostasis phase is followed by the inflammation phase.

The inflammation phase induces vasodilation and results in an influx of lymphocytes and macrophages. Macrophages will release growth factors, such as platelet-derived growth factor (PDGF), fibroblast growth factor (FGF), transforming growth factor-β (TGF-β), vascular endothelial growth factor (VEGF), interleukin-1 (IL-1), epidermal growth factor (EGF), and basic fibroblast growth factor (bFGF) that stimulate fibroblasts cells to promote the proliferation phase.

As the proliferative phase progresses, these growth factors stimulate angiogenesis and fibroplasias to rebuild blood flow to tissues after injury. Finally, the tissues mature to complete the wound healing processes. The tissue maturation phase also requires growth factors to control cell differentiation.

Because the wound healing processes involve multiple phases that require different factors at different times, any improper action of these factors in any phase may result in improper wound healing. For example, excessive fibrosis may lead to undesirable scar formation.

Given these multiple factors and their spatial and temporal interactions, identifying an appropriate drug treatment strategy is challenging. For effective controls of dermal wound healing, a therapy may need to modulate more than one phase and target for a positive wound repair outcome.

SUMMARY OF THE INVENTION

Embodiments of the present invention relate to compositions and methods for preventing and/or modulating the formation of dermal fibrotic disorders. Embodiments of the invention are based on therapeutic utilities of compounds possessing certain spectrum of pharmacologic effects to modulate exuberant activities in various phases of wound healing, thereby preventing and/or alleviating aberrant fibrotic tissue formations (e.g., scar formations). Specifically, compounds of the invention include agents that can interfere with multiple phases (multiple targets) of wound healing processes. These agents will be referred to as "multi-phase modulators" or "multi-target modulators." The "multi-phase modulators" or "multi-target modulators" may include multikinase inhibitors that can inhibit multiple kinases, as well as soluble guanylate cyclase (SGC) stimulators that can stimulate the activities of soluble guanylate cyclase.

In one aspect, embodiments of the invention relate to methods for preventing and/or modulating formation of a dermal fibrotic disorder. A method in accordance with embodiments of the invention includes administering a therapeutically effective amount of a multi-phase modulator to a subject in need thereof. The subject may be a mammal, particularly a human.

In accordance with embodiments of the invention, a multi-phase modulator may be a multiple-kinase ("multikinase") inhibitor or a soluble guanylate cyclase (SGC) stimulator (e.g., riociguat). As used herein, the term a "multikinase inhibitor" refers to a compound that can inhibit multiple kinases, particularly multiple receptor tyrosine kinases. A soluble guanylate cyclase (SGC) stimulator can stimulate the activity of an SGC, leading to the formation of cyclic GMP (cGMP), which is a second messenger in various signal transduction pathways.

In accordance with embodiments of the invention, a multikinase inhibitor, for example, may include axitinib, nintedanib, sorafenib, sunitinib or lenvatinib, which can inhibit receptor tyrosine kinases, such as VEGFR receptors (VEGFR-1, VEGFR-2, and/or VEGFR-3) and PDGF receptors (PDGFR1 and/or PDGFR2). In addition, compounds of the invention (e.g., axitinib, nintedanib, sorafenib, sunitinib, and lenvatinib) also have various degrees of inhibitory potencies against fibroblast growth factor receptors (FGFR).

In accordance with embodiments of the invention, the multikinase inhibitors may include, but are not limited to, axitinib, nintedanib, sorafenib, sunitinib, lenvatinib, panatinib, pazopanib, regorafenib, and their stereoisomer, tautomer, prodrug, free base, analogs, metabolites, pharmaceutically acceptable salt, solvate or solvate of a salt thereof. These compounds have anti-multikinase activities, such as anti-VEGFR, anti-PDGFR, and/or anti-FGFR activities. As shown in this description, these multikinase inhibitors can inhibit exuberant tissue fibrosis or scar formation. They are effective in remedying undesired scar formation, presumably due to their abilities to inhibit multiple kinases, such as receptor tyrosine kinases that mediate signal transductions in the various phases of wound healing, thereby modulating the wound healing processes at multiple phases.

As used herein, a "pharmaceutically acceptable salt" refer to a compound that has been modified by adding an acid or base to make a salt thereof, wherein the compound may be a parent compound, or a prodrug, a derivative, a metabolite, or an analog of the parent compound.

In accordance with some embodiments of the invention, the multikinase inhibitor is axitinib. Axitinib is a tyrosine kinase inhibitor of VEGFR-1, VEGFR-2 and VEGFR-3. Axitinib has been shown to potently inhibit VEGF-mediated endothelial cell proliferation and survival. Axitinib also inhibits closely related receptor tyrosine kinases (RTKs), such as PDFGR-1, PDGFR-2, and KIT.

In accordance with some embodiments of the invention, the multikinase inhibitor is nintedanib. Nintedanib is tyrosine kinase inhibitor of various receptors, such as VEGFR, FGFR, PDGFR-α and PDGFR-β, and FGF.

In accordance with some embodiments of the invention, the multikinase inhibitor is sorafenib. Sorafenib is a tyrosine kinase inhibitor of several receptors, such as VEGFR-2, VEGFR-3 and PDGFR2

In accordance with some embodiments of the invention, the multikinase inhibitor is sunitinib. Sunitinib is tyrosine kinase inhibitor of VEGFR and PDGFR.

In accordance with some embodiments of the invention, the multikinase inhibitor is lenvatinib. Lenvatinib is a tyrosine kinase receptor inhibitor of various receptors, such as VEGFR-1, VEGFR-2, VEGFR-3, FGFR-1, FGFR-2, FGFR-3, FGFR-4, and PDGFR-α.

In accordance with some embodiments of the invention, the multi-phase modulator is an SGC stimulator, such as riociguat. Riociguat, a soluble guanylate cyclase stimulator, may have effects on proliferation, fibrosis and inflammation in wound healing.

In accordance with embodiments of the invention, an agent for controlling exuberant activities in various phases of wound healing may be used with other types of agents that can interfere with one or more phases involved in wound healing. These other agents may include anti-angiogenic agents, anti-inflammatory agents, or anti-vascular permeability agents. Preferred anti-angiogenic agents include, but are not limited to, tyrosine kinase inhibitors, in particular, those targeting multiple receptors, such as those described in further detail herein: angiostatic cortisenes; matrix metalloprotease inhibitors; integrin inhibitors; PDGF antagonists; anti-proliferatives; hypoxia inducible factor-I inhibitors; fibroblast growth factor inhibitors; epidermal growth factor inhibitors; tissue inhibitor of metalloproteinases inhibitors; insulin-like growth factor inhibitors; tumor necrosis factor inhibitors; antisense oligonucleotides; anti-VEGF antibody, VEGF trap, anti-VEGF and/or anti-PDGF compounds, and their stereoisomer, tautomer, prodrug, free base, analogs, metabolites, pharmaceutically acceptable salt, solvate or solvate of a salt thereof.

In accordance with embodiments of the invention, the dermal fibrotic disorders include but not limited to acne scars, skin scars such as keloids and hypertrophic scars, wrinkles, cellulite and dermal neoplastic fibrosis, scarring alopecia, various vasculopathy, vasculitis, burn wound healing, diabetic foot syndrome, scleroderma, arthrofibrosis, peyronie's disease, dupuytren's contracture, or adhesive capsulitis.

In accordance with embodiments of the invention, compounds/molecules of the present invention may be administered by oral, parenteral, buccal, vaginal, rectal, inhalation, insufflation, sublingual, intramuscular, intradermal, subcutaneous, topical, intranasal, intraperitoneal, intrathoracic, intralesional, paralesional, intravenous, epidural, intrathecal, or intracerebroventricular routes, or by injection into the tissue and/or joints.

DETAILED DESCRIPTION

Figure 1:
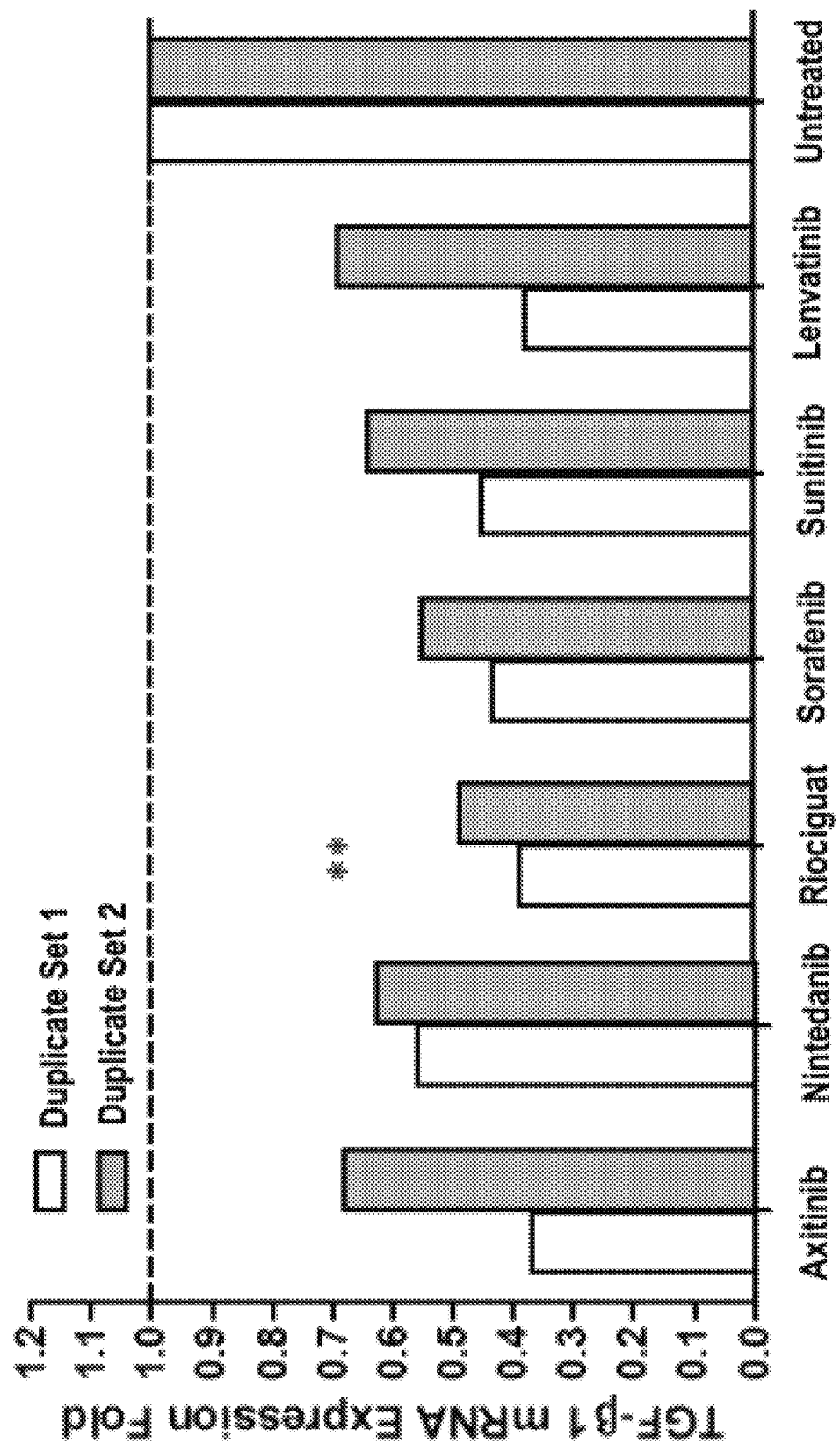
FIG. 1 shows TGF-β1 mRNA expression levels in wound sites treated with compounds of the invention relative to those in an untreated unwounded site on the dorsum of pigs.

Embodiments of the present invention relate to compositions (multi-phase modulators) and methods for preventing and/or modulating the formation of dermal fibrotic disorders. Dermal wound healing involves several phases: hemostasis, inflammation, proliferation, and tissue maturation. The overall process is induced and regulated by a complex array of factors, such as growth factors and cytokines. Effective approaches to the control of exuberant activities in would healing likely require controls and modulations in multiple phases.

Factors involved in wound healing exert their functions by binding to their respective receptors to activate various signaling pathways. These receptors include tyrosine kinases. Therefore, receptor tyrosine kinase inhibitors (particularly multikinase inhibitors) can be used to regulate the exuberant wound healing processes. Embodiments of the invention are based on therapeutic utilities of compounds that possess a certain spectrum of pharmacologic effects to modulate exuberant activities in various phases of wound healing, thereby preventing and/or alleviating aberrant fibrotic tissue formations (e.g., scar formations).

Because various kinases are involved in different phases of the wound healing processes, compounds of the invention include multikinase inhibitors that can inhibit multiple kinases, thereby interfering with multiple kinase-mediated signaling pathways. By inhibiting multiple kinases, one can achieve overall effects that may not be achievable by inhibiting a single kinase. In other words, by inhibiting multiple kinases in multiple phases of the wound healing processes, one may be able to achieve therapeutically effective effects to have a meaningful control of the undesirable fibrosis.

Compounds of the invention, for example, may include axitinib, nintedanib, sorafenib, sunitinib, lenvatinib, panatinib, pazopanib, and regorafenib, which can potently inhibit receptor tyrosine kinases, such as VEGFR receptors (VEGFR-1, VEGFR-2, and/or VEGFR-3) and/or PDGF receptors (PDGFR1 and/or PDGFR2). In addition, these compounds also have different extents of inhibitory potencies against fibroblast growth factor receptors (FGFR). Having the abilities to inhibit multiple receptor tyrosine kinases (e.g., VEGFR, PDGFR, and/or FGFR), these compounds can produce effective controls of undesirable fibrosis, such as in scar formation.

In addition to multikinase inhibitors, soluble guanylate cyclase (SGC) stimulators may also be used in embodiments of the invention. SGC stimulators may also interfere with multiple phases of wound healing. Thus, in accordance with some embodiments of the invention, a compound of the invention may be an SGC stimulator, such as riociguat.

As used herein, the term "dermal fibrotic disorder" refers to exuberant activities in various phases of wound healing that would result in aberrant fibrotic tissue formations (e.g., scar formations).

As used herein, the term a "therapeutic effective amount" is an amount that would achieve the desired therapeutic effects. A therapeutic effective amount would depend on the patient conditions, routes of administration, administration regimes etc. One skilled in the art would be able to determine a therapeutic effective amount without inventive efforts.

The following describes some specific examples to illustrate embodiments of the invention. One skilled in the art would appreciate that these examples are for illustration only and other modifications and variations are possible without departing from the scope of the invention.

EXPERIMENT #1

Porcine skin resembles human skin in many aspects. Both species have a relatively thick epidermis, distinct rete pegs, dermal papillae, and dense elastic fibers in the dermis. Furthermore, unlike rodents and rabbits, porcine skin is adherent to the subcutaneous structures, similar to human skin. Because of these anatomical similarities and other parallelisms in wound healing, porcine models have emerged as important foundations for the study of pathophysiology and potential treatment paradigms for abnormal wound healing. It has also been observed in porcine full-thickness wound healing in Yucatan Minipigs that the spatial and temporal expressions of TGF-B1, PDGF and VEGF were similar to the patterns for the growth factors described above. Therefore, the full-thickness excision models in Yucatan minipigs are the models for human wound healing studies.

In this experiment, multiple full-thickness excision wounds were made to the dorsum of Yucatan minipigs, and the wound sites were allowed to re-epithelialized adequately. At four weeks post-wound, the wound sites had normal to pink vascularity and had pliability. Epidermal hyperplasia was observed, as expected for regenerative responses in the full-thickness wounds.

On Day 28 post-wound, a dose (e.g., 1%) of axitinib, nintedanib, riociguat, sorafenib, sunitinib, and/or lenvatinib was administered into the dermal tissue at or around the wound sites, once every two weeks on two occasions. One wound site was left untreated as the control for each pig. Please note that the particular parameters in this example are only for illustration. One skilled in the art would appreciate that the dosages, administration methods, treatment regimen, and the administration sites may be varied to achieve similar results.

On Day 59 post wound, the minipigs were sacrificed and dermal tissues were collected for qualitative and quantitative evaluation using hematoxylin and eosin, and Mason's Trichrome staining. Dermal fibroplasia was characterized by increased numbers of fibroblasts in the dermis suspended in variable amounts of collagen in wounds.

In addition, total mRNA was isolated from skin biopsies of the treated wound sites and the untreated unwounded sites of the pigs. The mRNA samples were used to prepare cDNA and analyzed via qRT-PCR. The TGF-β1 expression levels were assessed using beta actin as a reference gene.

Transforming-growth-factor (TGF)-β expression, following inflammatory responses, results in increased production of extracellular matrix (ECM) components, as well as mesenchymal cell proliferation, migration, and accumulation. Therefore, TGF-β has been found to induce fibrosis associated with chronic phases of inflammatory diseases. As shown in FIG. 1, compounds of the invention significantly reduced the expression levels of TGF-β1, suggesting that compounds of the invention can be used to control undesired fibrosis.

The histologic evaluation results, shown in Table 1, indicate that these compounds are effective in controlling the undesirable neovascular and fibrotic formation.

Among the various test compounds administered as two biweekly treatments, axitinib and nintedanib noticeably reduced neovascularization with a corresponding reduced dermal fibroplasia, as assessed by histopathologic examinations of the treated wounds relative to the untreated wound (Table. 1).

Figure 2:
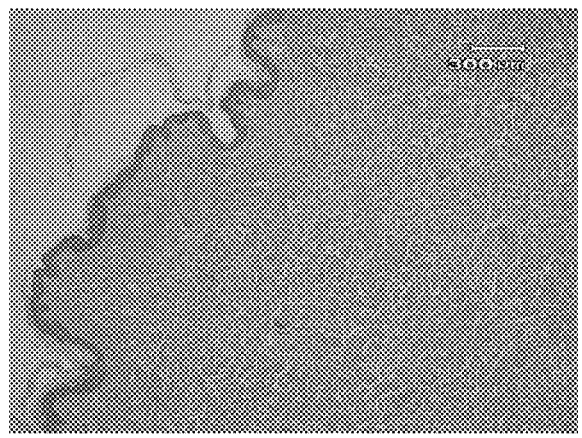
FIG. 2 shows images of pig dermal tissues from histologic slides after hematoxylin and eosin staining. There was a decrease in neovascularization and fibrosis in drug treatment groups as compared to the untreated wound control. Panel (A) unwounded normal skin. Panel (B) untreated wound tissue, showing more neovascularization and fibrosis. Panel (C) axitinib treated wound, showing neovascularization and reduced fibrosis.
Figure 2:
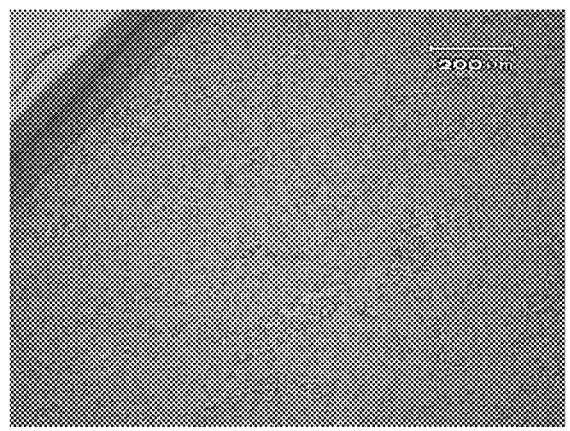
Figure 2:
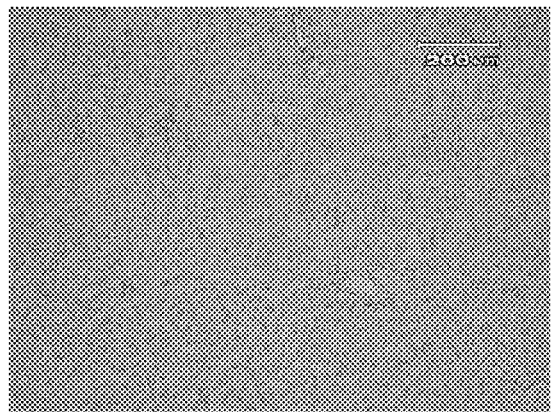

FIG. 2 shows exemplary hematoxylin and eosin stainings of pig dermal tissues from treated and untreated wound sites. Panel (A) show a staining from an unwounded skin as a control. Panel (B) shows a staining of a sample from a wounded site without treatment with any compound of the invention. It is evident that the wounded tissue has substantial neovascularization and fibrosis. Panel (C) shows a staining of a sample from a wounded site treated with axitinib. Axitinib treatment results in significantly reduced neovascularization and reduced fibrosis, as compared with the untreated wound (see Panel (B)). These results clearly show that compounds of the invention are effective in reducing neovascularization and fibrosis at the wounded sites. As a result, compounds of the invention may be used to reduce undesired fibrosis, such as scar formation.

TABLE 1

Qualitative assessments of dermal fibroplasia and neovascularization at wound sites after two doses. (minimal = 1, mild = 2, moderate = 3, marked = 4, and severe = 5)

| | Individual Scores & Average Scores (bolded) | | | | | | |
|---|---|---|---|---|---|---|---|
| Finding | axitinib | nintedanib | riociguat | sorafenib | sunitinib | lenvatinib | untreated |
| Fibroplasia; dermis | 2, 2, 3 (2.33) | 3, 2, 2 (2.33) | 3, 2, 3 (2.67) | 3, 3, 3 (3.00) | 3, 3, 2 (2.67) | 3, 3, 3 (3.00) | 3, 3, 4 (3.33) |
| Neovascularization; dermis | 1, 2, 2 (1.67) | 2, 2, 1 (1.67) | 3, 2, 3 (2.67) | 2, 2, 3 (2.33) | 2, 3, 2 (2.33) | 2, 3, 2 (2.33) | 3, 1, 3 (2.33) |

As shown in Table 2, compounds of the invention also resulted in reduction of TGF-β1 mRNA expression levels at the treated wounds, as compared to the expression level in unwounded normal skin, suggesting that compounds of the invention can be used to control the exuberant fibrosis. Among these compounds, axitinib, nintedanib, riociguat, sorafenib, and sunitinib are the most effective.

TABLE 2

TGF-β1 mRNA expression in Yucatan pig skin wound sites after treatments.

TGF-β1 mRNA Expression Fold Relative to Untreated Unwounded Control

| Animal Number | Duplicate Set | axitinib | nintedanib | riociguat | sorafenib | sunitinib | lenvatinib |
|---|---|---|---|---|---|---|---|
| 7369 | 1 | 0.37 | 0.56 | 0.39 | 0.43 | 0.45 | 0.38 |
|  | 2 | 0.68 | 0.63 | 0.49 | 0.55 | 0.64 | 0.69 |
| 7370 | 1 | 0.78 | 0.87 | 0.8 | 0.89 | 1.86 | 2.02 |
|  | 2 | 0.89 | 0.70 | 0.60 | 0.84 | 0.50 | 2.27 |
| 7371 | 1 | 0.68 | 0.66 | 0.76 | 0.60 | 0.53 | 0.62 |
|  | 2 | 0.64 | 0.55 | 0.87 | 0.53 | 0.48 | 0.89 |

EXPERIMENT #2

In rabbits, wounds are created down to the bare cartilage on the ventral surface of the ear using a dermal biopsy punch. Because these wounds do not heal by contraction, epithelialization is delayed and a raised scar is created. By both appearance and histological analysis, these scars resemble human hypertrophic scars. In this established model, it was shown that reduced TGF-β expression results in reduced scarring, which is consistent with the current understanding of the pathogenesis of excessive scarring/dermal fibrosis. Furthermore, excessive angiogenesis and vascularization have been shown to result in pathological hypertrophic scar in this model. Thus, this rabbit model was also used to assess the compounds of the invention.

Eight wounds were created on the ventral surface of the ears of each of New Zealand White rabbits using skin punch biopsies, and then the wounds were allowed to heal for approximately 2 weeks.

A dose (e.g., 1%) of axitinib, nintedanib, riociguat, sorafenib, sunitinib, and/or lenvatinib was administered into the dermal tissue, once every two weeks on two occasions. Again, the specific doses, treatment methods and schedules are for illustration only. One skilled in the art would appreciate that variations and modifications are possible to achieve similar results.

On Day 42 post wound, the rabbits were sacrificed and dermal tissues were collected for qualitative and quantitative evaluation using hematoxylin and eosin and Mason's Trichrome staining. In addition, TGF-β1 mRNA expression levels were measured using qRT-PCR.

Histologic slides for hematoxylin and eosin stainings were prepared from the wound sites. Tissues were evaluated qualitatively for inflammation, neovascularization, granulation tissue, degrees of re-epithelialization, and degrees of scarring (avascular collagen).

As compared with untreated wound and the vehicle-treated wound, the wounds treated with nintedanib had much less neovascularization and less scar tissues. As compared with the vehicle-treated wound, the mean TGFb1 mRNA level was lower after intradermal treatment with nintedanib.

Figure 3:
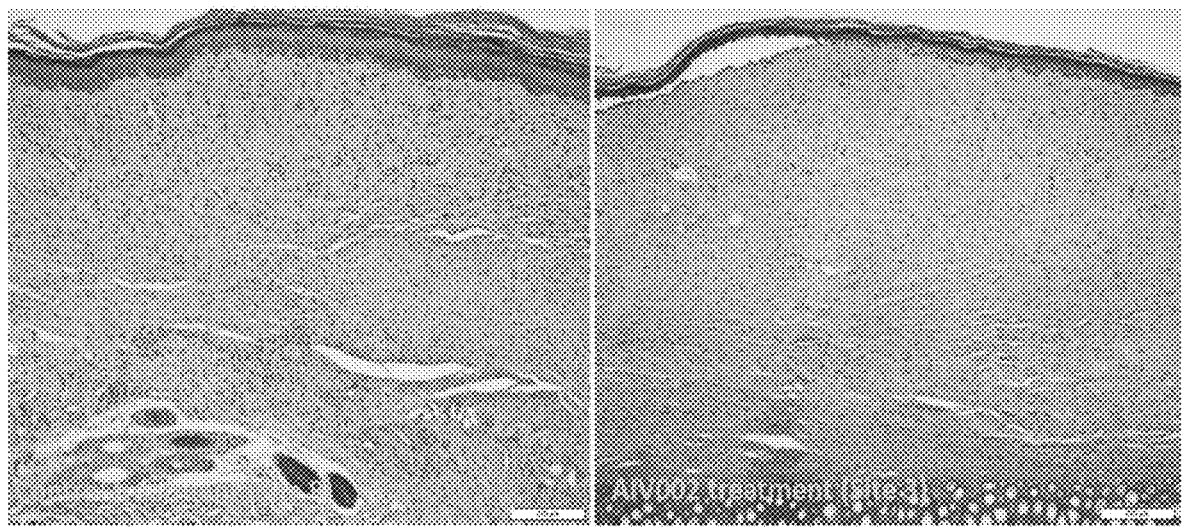
FIG. 3 shows results of nintedanib (labeled as AIV002) treatment of rabbit ear hypertrophic scar. Nintedanib treatment decreased neovascularization and dermal fibrosis. Panel (A) shows H&E staining (left: untreated; right: treated wound), wherein the untreated site has substantial neovascularization (left), relative to the treated site (right). Panel (B) shows Mason's Trichrome staining (left: untreated; right treated wound).
Figure 3:
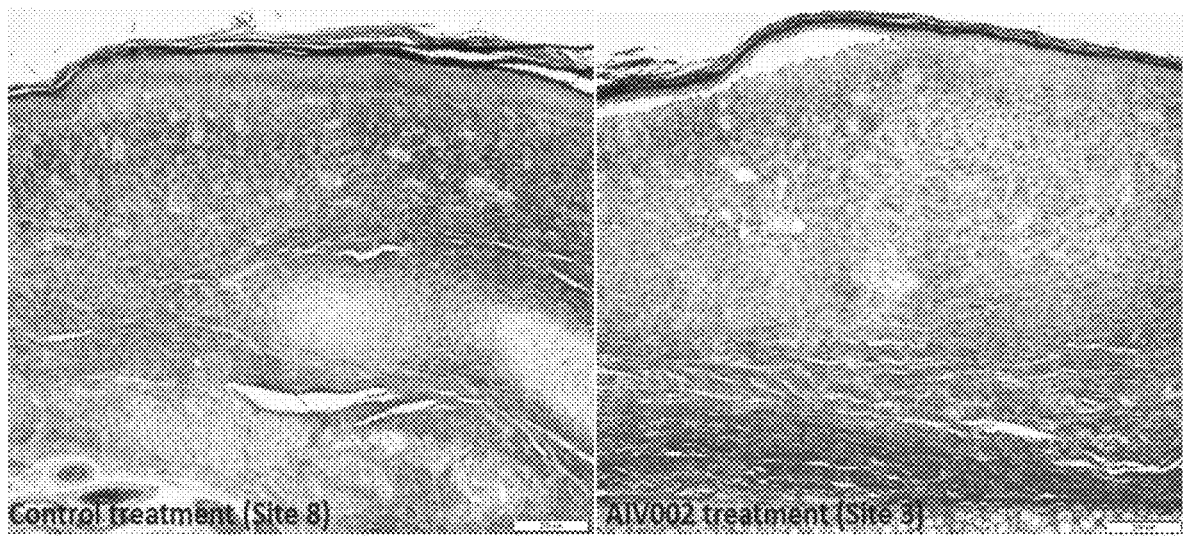
Figure 4:
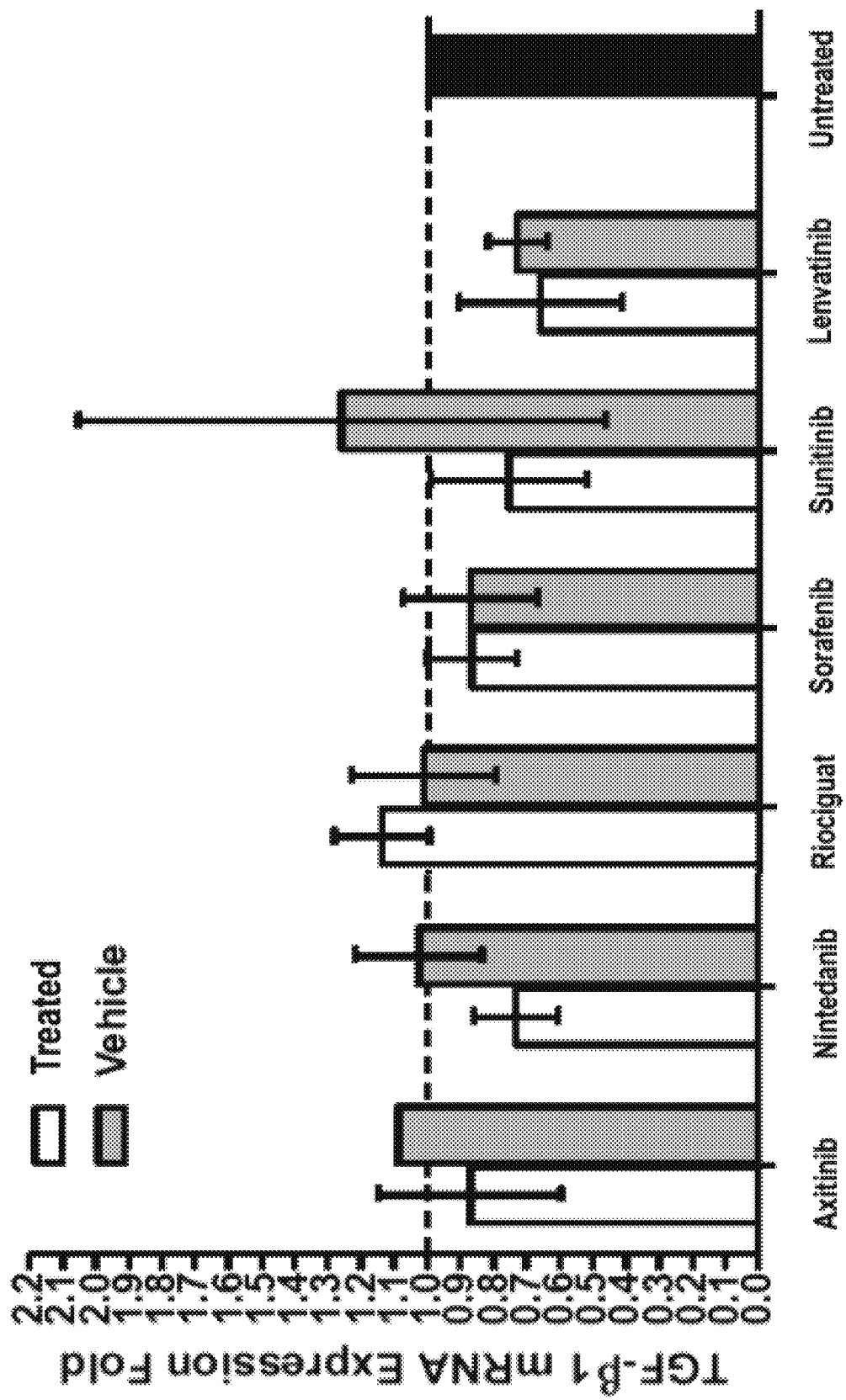

FIG. 3 shows results of nintedanib (labeled as AIV002) treatment of rabbit ear hypertrophic scar. Nintedanib treatment decreased neovascularization and dermal fibrosis. Panel (A) shows H&E staining (left: untreated; right: treated wound), wherein the untreated site has substantial neovascularization (left), relative to the treated site (right). Panel (B) shows Mason's Trichrome staining (left: untreated; right treated wound).

In addition to nintedanib, other compounds of the invention also have similar effects. For example, as compared with the untreated wound and the vehicle-treated wound, the wounds treated with axitinib had less neovascularization, less fibrosis, and less scar tissues. As compared with the vehicle-treated wound, the mean TGFb1 mRNA level was lower after intradermal treatment with axitinib.

As compared with untreated wound and the vehicle-treated wound, the wounds treated with riociguat had slightly decreased neovascularization and fibrosis.

As compared with untreated wound and the vehicle-treated wound, the wounds treated with sorafenib had slightly increased neovascularization, and similar or decreased fibrosis. As compared with vehicle-treated wound, the mean TGFb1 mRNA level was lower after intradermal treatment with sorafenib.

As compared with untreated wound and the vehicle-treated wound, the wounds treated with sunitinib had more neovascularization, and similar fibrosis. As compared with the vehicle-treated wound, the mean TGFb1 mRNA level was lower after intradermal treatment with sunitinib.

As compared with untreated wound and the vehicle-treated wound, intradermal treatment with lenvatinib had similar neovascularization, fibrosis, and re-epithelialization. As compared with the vehicle-treated wound, the mean TGFb1 mRNA level was lower after intradermal treatment with lenvatinib.

TABLE 3

TGF-β1 mRNA expression in rabbit ear wound sites after intradermal treatments.

Rabbit TGFB1 mRNA Expression Fold by Treatment Relative to Untreated Wounded (mean ± SD)

| Group | N | axitinib | nintedanib | riociguat | sorafenib | sunitinib | lenvatinib |
|---|---|---|---|---|---|---|---|
| Normal skin | 3 | | | 0.61 ± 0.15 | | | |
| Untreated (all rabbits) | 7 | | | 1.00 | | | |
| Treated (each drug) | 5 or 6 | 0.87 ± 0.28 | 0.73 ± 0.13 | 1.14 ± 0.14 | 0.87 ± 0.13 | 0.76 ± 0.23 | 0.66 ± 0.25 |

TABLE 3-continued

TGF-β1 mRNA expression in rabbit ear wound sites after intradermal treatments.

| Group | N | Rabbit TGFB1 mRNA Expression Fold by Treatment Relative to Untreated Wounded (mean ± SD) | | | | | |
|---|---|---|---|---|---|---|---|
| | | axitinib | nintedanib | riociguat | sorafenib | sunitinib | lenvatinib |
| Vehicle (each drug) | 1 or 2 | 1.09 | 1.03 ± 0.19 | 1.01 ± 0.22 | 0.87 ± 0.20 | 1.26 ± 0.79 | 0.73 ± 0.09 |

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for modulating formation of a dermal fibrotic disorder, comprising:
administering to a subject a therapeutically effective amount of multi-kinase inhibitor selected from the group consisting of axitinib, sunitinib, ponatinib, and a combination thereof;
wherein said dermal fibrotic disorder is aberrant wound-healing, wrinkle, cellulite and dermal neoplastic fibrosis, vasculopathy, vasculitis, exuberant burn wound-healing, diabetic foot syndrome, scleroderma, arthrofibrosis, or Peyronie's disease.

2. The method according to claim 1, wherein the subject is a human.

3. The method according to claim 1, wherein the administering is by intramuscular injection, intradermal injection, intralesional injection, subcutaneous injection, topical application, localized administration or by injection into a joint.

4. The method according to claim 1 wherein the multi-kinase inhibitor is axitinib.

5. The method according to claim 4, wherein the dermal fibrotic disorder is aberrant wound-healing.

6. The method according to claim 1, wherein the multi-kinase inhibitor is sunitinib.

7. The method according to claim 1, wherein the multi-kinase inhibitor is ponatinib.

8. The method according to claim 1, wherein the dermal fibrotic disorder is aberrant wound-healing.

9. The method according to claim 1, wherein the dermal fibrotic disorder is wrinkle.

10. The method according to claim 1, wherein the dermal fibrotic disorder is cellulite and dermal neoplastic fibrosis.

11. The method according to claim 1, wherein the dermal fibrotic disorder is vasculopathy.

12. The method according to claim 1, wherein the dermal fibrotic disorder is vasculitis.

13. The method according to claim 1, wherein the dermal fibrotic disorder is exuberant burn wound-healing.

14. The method according to claim 1, wherein the dermal fibrotic disorder is diabetic foot syndrome.

15. The method according to claim 1, wherein the dermal fibrotic disorder is scleroderma.

16. The method according to claim 1, wherein the dermal fibrotic disorder is arthrofibrosis.

17. The method according to claim 1, wherein the dermal fibrotic disorder is Peyronie's disease.

* * * * *